United States Patent
Hirota (10) Patent No.: US 11,333,599 B2
(45) Date of Patent: May 17, 2022

(54) PHOTOACOUSTIC IMAGE GENERATION APPARATUS, PHOTOACOUSTIC IMAGE GENERATION METHOD, AND PHOTOACOUSTIC IMAGE GENERATION PROGRAM

(71) Applicant: FUJIFILM Corporation, Tokyo (JP)

(72) Inventor: Kazuhiro Hirota, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 454 days.

(21) Appl. No.: 16/417,999

(22) Filed: May 21, 2019

(65) Prior Publication Data

US 2019/0271638 A1 Sep. 5, 2019

Related U.S. Application Data (63) Continuation of application No. PCT/JP2017/037097, filed on Oct. 13, 2017.

(30) Foreign Application Priority Data

Dec. 22, 2016 (JP) .............................. JP2016-249707

(51) Int. Cl.
  *G01N 21/17* (2006.01)
  *A61B 5/00* (2006.01)
  *A61B 8/13* (2006.01)

(52) U.S. Cl.
  CPC ....... *G01N 21/1702* (2013.01); *A61B 5/0095* (2013.01); *A61B 8/13* (2013.01)

(58) Field of Classification Search
  None
  See application file for complete search history.

(56) References Cited

U.S. PATENT DOCUMENTS

| | | | | |
|---|---|---|---|---|
| 2014/0182383 | A1* | 7/2014 | Suzuki | G16H 30/00 73/655 |
| 2017/0100041 | A1 | 4/2017 | Kasamatsu et al. | |
| 2017/0332909 | A1* | 11/2017 | Nagae | A61B 8/4494 |

FOREIGN PATENT DOCUMENTS

| | | |
|---|---|---|
| JP | 5-253220 A | 10/1993 |
| JP | 2000-201933 A | 7/2000 |

(Continued)

OTHER PUBLICATIONS

Kostli et al., "Two-dimensional photoacoustic imaging by use of Fourier-transform image reconstruction and a detector with an anisotropic response" Applied Optics, 2003, vol. 42, No. 10, pp. 1899-1909. (Year: 2003).*

(Continued)

*Primary Examiner* — Yi-Shan Yang
(74) *Attorney, Agent, or Firm* — Birch, Stewart, Kolasch & Birch, LLP (57) ABSTRACT

Provided are a photoacoustic image generation apparatus, a photoacoustic image generation method, and a photoacoustic image generation program that can perform a more appropriate reconstruction process regardless of the type of probe, without causing a reduction in the speed of an arithmetic process. It is identified whether a probe that detects photoacoustic waves and outputs a photoacoustic wave detection signal is a probe in which detection elements are arranged by a coordinate system using polar coordinates or a probe in which detection elements are arranged by a rectangular coordinate system. In a case in which the probe is identified as the probe in which the detection elements are arranged by the coordinate system using the polar coordinates, a time domain reconstruction process is selected to generate a photoacoustic image.

20 Claims, 5 Drawing Sheets

(56) References Cited

FOREIGN PATENT DOCUMENTS

| | | |
|---|---|---|
| JP | 2001-104304 A | 4/2001 |
| JP | 2007-14485 A | 1/2007 |
| JP | 2010-35806 A | 2/2010 |
| JP | 2014-140717 A | 8/2014 |
| WO | WO 2015/198548 A1 | 12/2015 |

OTHER PUBLICATIONS

Japanese Office Action for corresponding Japanese Application No. 2018-557563, dated Jul. 14, 2020, with English translation.
Japanese Office Acton, dated Apr. 14, 2020, for corresponding Japanese Application No. 2018-557563, with an English translation.
International Preliminary Report on Patentability and Written Opinion of the International Searching Authority (Forms PCT/IB/326, PCT/IB/373, and PCT/ISA/237) for International Application No. PCT/JP2017/037097, dated Jul. 4, 2019, with English translation.
International Search Report (Form PCT/ISA/210) for International Application No. PCT/JP2017/037097, dated Nov. 14, 2017, with English translation.

* cited by examiner

PHOTOACOUSTIC IMAGE GENERATION APPARATUS, PHOTOACOUSTIC IMAGE GENERATION METHOD, AND PHOTOACOUSTIC IMAGE GENERATION PROGRAM

CROSS-REFERENCE TO RELATED APPLICATIONS

This application is a Continuation of PCT International Application No. PCT/JP2017/037097 filed on Oct. 13, 2017, which claims priority under 35 U.S.C. § 119(a) to Japanese Patent Application No. 2016-249707 filed on Dec. 22, 2016. Each of the above application(s) is hereby expressly incorporated by reference, in its entirety, into the present application.

BACKGROUND OF THE INVENTION

1. Field of the Invention

The present invention relates to a photoacoustic image generation apparatus, a photoacoustic image generation method, and a recording media storing non-transitory computer readable photoacoustic image generation program that detect photoacoustic waves generated in a subject irradiated with light and generate a photoacoustic image.

2. Description of the Related Art

In recent years, photoacoustic imaging has been known which captures the image of the inside of a living body using a photoacoustic effect. In general, in the photoacoustic imaging, the inside of the living body is irradiated with pulsed laser light. In the inside of the living body, a living body tissue absorbs the energy of the pulsed laser light and ultrasonic waves (photoacoustic waves) are generated by adiabatic expansion caused by the energy. For example, an ultrasound probe detects the photoacoustic waves and a photoacoustic image is formed on the basis of a detection signal. In this way, it is possible to visualize the inside of the living body on the basis of the photoacoustic waves.

Here, in a case in which a photoacoustic image is generated in the photoacoustic imaging, a reconstruction process is performed for the detection signal detected by the ultrasound probe. A frequency domain reconstruction process, such as a reconstruction process using a Fourier transform algorithm (FTA) method, or a time domain reconstruction process, such as a reconstruction process using a delay-and-sum (DnS) method, has been proposed as the reconstruction process (for example, see JP2010-035806A). In a case in which the reconstruction process using the FTA method is compared to the reconstruction process using the DnS method, the amount of calculation in the reconstruction process using the FTA method is less than that in the reconstruction process using the DnS method and the quality of a photoacoustic image in the reconstruction process using the FTA method is higher than that in the reconstruction process using the DnS method. The reconstruction process using the FTA method uses the dispersion relation of photoacoustic waves in a frequency space to simply connect a time frequency space and a spatial frequency space. Therefore, the detected time-space information can be converted into real-space information by a simple arithmetic process.

SUMMARY OF THE INVENTION

However, an arithmetic process of the reconstruction process using the FTA method is performed for a detection signal of a probe in which detection elements are arranged by a rectangular coordinate system such as a linear probe. Therefore, it is difficult to use the arithmetic process of the reconstruction process using the FTA method for a detection signal of a probe in which detection elements are arranged by coordinate systems other than the rectangular coordinate system, such as a convex probe, without any change. Even in a case in which the arithmetic process is changed, the arithmetic process becomes very complicated and the amount of calculation increases, which makes it difficult to perform the reconstruction process at a high speed.

The invention has been made in view of the above-mentioned problems and an object of the invention is to provide a photoacoustic image generation apparatus, a photoacoustic image generation method, and a recording media storing non-transitory computer readable photoacoustic image generation program that can perform a more appropriate reconstruction process regardless of the type of probe, without causing a reduction in the speed of an arithmetic process.

According to an aspect of the invention, there is provided a photoacoustic image generation apparatus comprising: a probe that detects photoacoustic waves generated in a subject irradiated with light and outputs a photoacoustic wave detection signal; a probe identification unit that identifies whether the probe is a probe in which detection elements are arranged by a coordinate system using polar coordinates or a probe in which detection elements are arranged by a rectangular coordinate system; and a photoacoustic image generation unit that performs a time domain reconstruction process or a frequency domain reconstruction process, using the photoacoustic wave detection signal, to generate a photoacoustic image. In a case in which the probe is identified as the probe in which the detection elements are arranged by the coordinate system using the polar coordinates, the photoacoustic image generation unit selects the time domain reconstruction process and generates the photoacoustic image.

In the photoacoustic image generation apparatus according to the aspect of the invention, the probe identification unit may identify at least one of a convex probe, a micro-convex probe, or a radial scanning probe as the probe in which the detection elements are arranged by the coordinate system using the polar coordinates.

In the photoacoustic image generation apparatus according to the aspect of the invention, in a case in which the probe is identified as the probe in which the detection elements are arranged by the rectangular coordinate system, the photoacoustic image generation unit may select the frequency domain reconstruction process and generate the photoacoustic image.

The photoacoustic image generation apparatus according to the aspect of the invention may further comprise a reconstruction process selection receiving unit that receives a selection of one of the time domain reconstruction process and the frequency domain reconstruction process in a case in which the probe is identified as the probe in which the detection elements are arranged by the rectangular coordinate system. The photoacoustic image generation unit may generate the photoacoustic image using the reconstruction process received by the reconstruction process selection receiving unit.

In the photoacoustic image generation apparatus according to the aspect of the invention, the probe identification unit may identify at least one of a linear probe or a sector probe as the probe in which the detection elements are arranged by the rectangular coordinate system.

In the photoacoustic image generation apparatus according to the aspect of the invention, the time domain reconstruction process may be a reconstruction process using a delay-and-sum (DnS) method.

In the photoacoustic image generation apparatus according to the aspect of the invention, the time domain reconstruction process may be a reconstruction process using a convolution back projection (CBP) method.

In the photoacoustic image generation apparatus according to the aspect of the invention, the frequency domain reconstruction process may be a reconstruction process using a Fourier transform algorithm (FTA) method.

In the photoacoustic image generation apparatus according to the aspect of the invention, the probe may detect reflected waves of acoustic waves transmitted to the subject and output a reflected wave detection signal. The photoacoustic image generation apparatus may further comprise a reflected wave image generation unit that performs the reconstruction process using the delay-and-sum (DnS) method on the basis of the reflected wave detection signal to generate a reflected wave image.

In the photoacoustic image generation apparatus according to the aspect of the invention, the reflected wave image generation unit may implement a process of generating the reflected wave image using hardware and the photoacoustic image generation unit may implement a process of generating the photoacoustic image using software.

In the photoacoustic image generation apparatus according to the aspect of the invention, the photoacoustic image generation unit may implement the time domain reconstruction process using hardware and may implement the frequency domain reconstruction process using software.

According to another aspect of the invention, there is provided a photoacoustic image generation method that performs a time domain reconstruction process or a frequency domain reconstruction process, using a photoacoustic wave detection signal obtained by detecting photoacoustic waves generated in a subject irradiated with light, to generate a photoacoustic image. The photoacoustic image generation method comprises: identifying whether a probe that detects the photoacoustic waves and outputs the photoacoustic wave detection signal is a probe in which detection elements are arranged by a coordinate system using polar coordinates or a probe in which detection elements are arranged by a rectangular coordinate system; and selecting the time domain reconstruction process and generating the photoacoustic image in a case in which the probe is identified as the probe in which the detection elements are arranged by the coordinate system using the polar coordinates.

According to still another aspect of the invention, there is provided a recording media storing non-transitory computer readable photoacoustic image generation program that causes a computer to function as: a photoacoustic image generation unit that performs a time domain reconstruction process or a frequency domain reconstruction process, using a photoacoustic wave detection signal obtained by detecting photoacoustic waves generated in a subject irradiated with light, to generate a photoacoustic image; and a probe identification unit that identifies whether the probe is a probe in which detection elements are arranged by a coordinate system using polar coordinates or a probe in which detection elements are arranged by a rectangular coordinate system. The photoacoustic image generation unit selects the time domain reconstruction process and generates the photoacoustic image in a case in which the probe is identified as the probe in which the detection elements are arranged by the coordinate system using the polar coordinates.

According to the photoacoustic image generation apparatus, the photoacoustic image generation method, and the recording media storing non-transitory computer readable photoacoustic image generation program of the invention, it is identified whether the probe that detects the photoacoustic waves and outputs the photoacoustic wave detection signal is a probe in which detection elements are arranged by a coordinate system using polar coordinates or a probe in which detection elements are arranged by a rectangular coordinate system. In a case in which the probe is identified as the probe in which the detection elements are arranged by the coordinate system using the polar coordinates, the time domain reconstruction process is selected and the photoacoustic image is generated. Therefore, it is possible to perform a more appropriate reconstruction process regardless of the type of probe, without causing a reduction in the speed of an arithmetic process.

DESCRIPTION OF THE PREFERRED EMBODIMENTS

Figure 1:
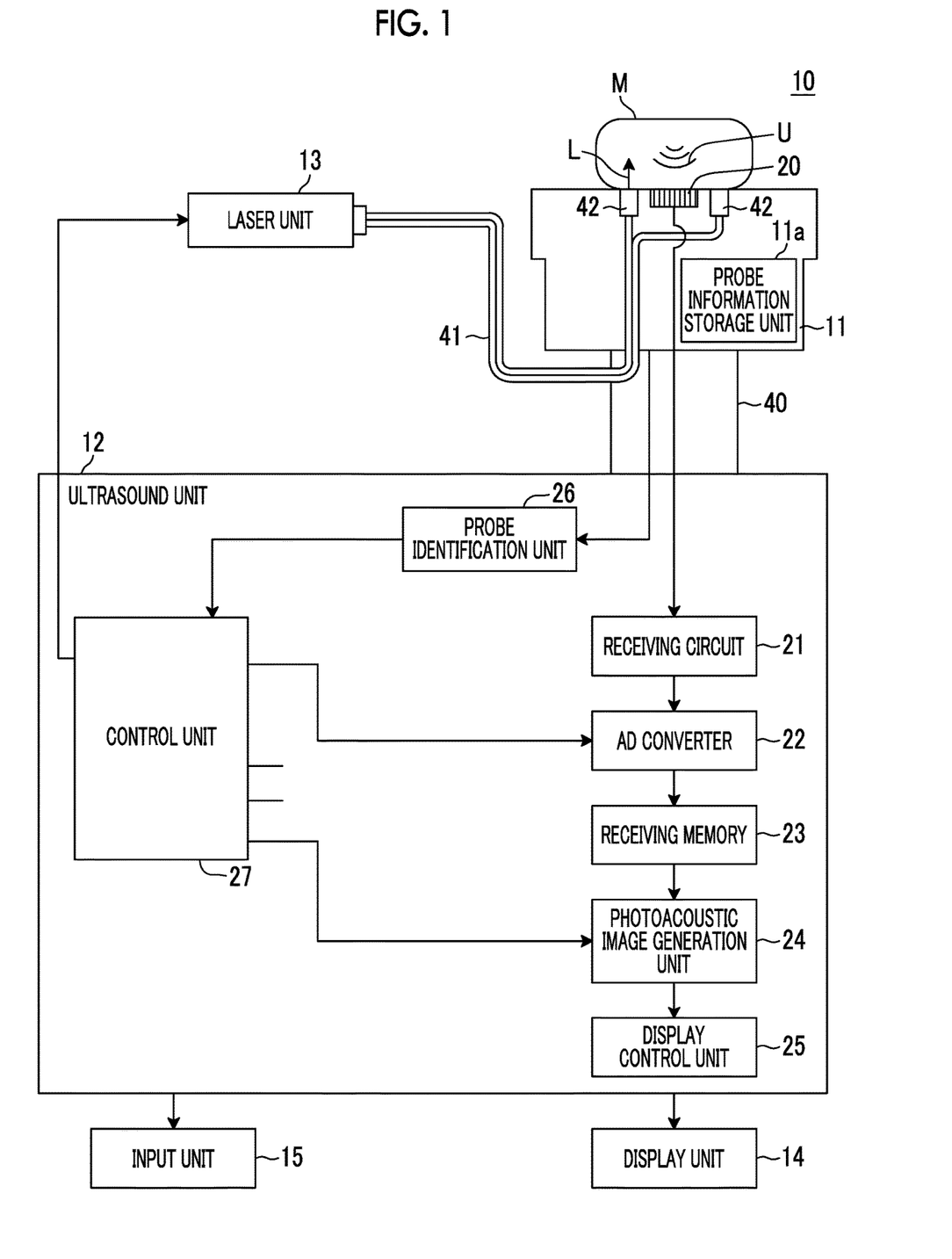
FIG. 1 is a block diagram schematically illustrating a configuration of an embodiment of a photoacoustic image generation apparatus according to the invention.

Hereinafter, an embodiment of a photoacoustic image generation apparatus according to the invention will be described with reference to the drawings. FIG. 1 is a diagram schematically illustrating the configuration of a photoacoustic image generation apparatus 10 according to this embodiment.

As illustrated in FIG. 1, the photoacoustic image generation apparatus 10 according to this embodiment comprises a probe 11, an ultrasound unit 12, a laser unit 13, a display unit 14, and an input unit 15.

The probe 11 is an ultrasound probe, detects photoacoustic waves U generated in a subject M, and outputs a photoacoustic wave detection signal. The probe 11 is connected to the ultrasound unit 12 through a cable 40 and is detachable from the ultrasound unit 12.

As illustrated in FIG. 1, the probe 11 comprises a transducer array 20, a bundle fiber 41 obtained by tying a plurality of optical fibers together, and two light emission portions 42 which are provided such that the transducer array 20 is interposed therebetween.

The transducer array 20 includes, for example, a plurality of ultrasound transducers which are one-dimensionally or two-dimensionally arranged. The ultrasound transducer corresponds to a detection element according to the invention and is, for example, a piezoelectric element which is made of a polymer film such as piezoelectric ceramics or polyvinylidene fluoride (PVDF). The ultrasound transducer has a function of converting a received signal into an electric signal in a case in which the photoacoustic waves U are received. The electric signal generated by the ultrasound transducer is output to a receiving circuit 21 which will be described below.

The bundle fiber 41 guides laser light from the laser unit 13 to the light emission portions 42. The bundle fiber 41 is not particularly limited and a known fiber, such as a quartz fiber, may be used. The bundle fiber 41 is branched into optical fibers on the light emission side and the optical fibers are connected to the light emission portions 42.

The light emission portions 42 irradiate the subject M with the laser light guided by the bundle fiber 41. As illustrated in FIG. 1, in this embodiment, the two light emission portions 42 are disposed on both sides of the transducer array 20 such that the transducer array 20 is interposed therebetween. For example, a light guide plate may be used as the light emission portion 42. For example, the light guide plate is a plate obtained by performing special processing on the surface of an acrylic plate or a quartz plate such that light incident from one end surface is uniformly emitted from the other end surface. It is preferable that the width of the transducer array 20 in an array direction is equal to the width of the light guide plate in order to uniformly illuminate the surface of the subject disposed on both sides of the transducer array 20. In addition, a diffusion plate may be provided at a light incident end or a light emission end of the light guide plate.

The probe 11 comprises a probe information storage unit 11a. The probe information storage unit 11a stores identification information of the probe 11. The identification information of the probe 11 is information that can identify whether the probe 11 is a probe in which ultrasound transducers (detection elements) are arranged by a rectangular coordinate system or a probe in which ultrasound transducers (detection elements) are arranged by a coordinate system using polar coordinates.

The arrangement of the ultrasound transducers by the rectangular coordinate system means that the ultrasound transducers are one-dimensionally or two-dimensionally arranged on a coordinate plane defined by the X-axis and the Y-axis which are orthogonal to each other. Examples of the probe in which the ultrasound transducers are arranged by the rectangular coordinate system include a linear probe and a sector probe in which ultrasound transducers are arranged on a straight line or a two-dimensional plane. In addition, hereinafter, the probe in which the ultrasound transducers are arranged by the rectangular coordinate system is simply referred to as a probe based on a rectangular coordinate system.

The coordinate system using polar coordinates is a coordinate system represented by a distance from the origin and an angle formed between a straight line connecting the origin and a point on a coordinate space and a coordinate axis and includes, for example, a polar coordinate system, such as circular coordinates system (R, θ) formed by a distance R and an angle θ, and spherical coordinates system (R, θ, φ) formed by the distance R and two angles θ and φ, and cylindrical coordinates system (R, θ, z) formed by the distance R, the angle θ, and a coordinate in the Z-axis direction. Examples of the probe in which the ultrasound transducers are arranged by the coordinate system using the polar coordinates include a convex probe and a microconvex probe in which the ultrasound transducers are arranged on an arc and a radial scanning probe in which the ultrasound transducers are arranged on the circumference of a circle. Hereinafter, the probe in which the ultrasound transducers are arranged by the coordinate system using the polar coordinates is simply referred to as a probe based on a coordinate system using polar coordinates.

For example, a semiconductor memory and an integrated circuit (IC) tag can be used as the probe information storage unit 11a. The identification information stored in the probe information storage unit 11a is read in response to a request signal from the ultrasound unit 12 in a case in which the probe 11 is connected to the ultrasound unit 12.

The configuration for storing the identification information of the probe 11 is not limited to the above. For example, a bar code may be provided in the probe 11 and the ultrasound unit 12 may acquire a signal obtained by reading the bar code. Alternatively, a mechanical structure, such as an uneven portion, may be provided in the probe 11. In a case in which the probe 11 is connected to the ultrasound unit 12, the ultrasound unit 12 may recognize the structure to acquire the identification information. In addition, a configuration in which the user sets and inputs the identification information of the probe 11 with the input unit 15 may be used.

A probe identification unit 26 of the ultrasound unit 12 acquires the identification information of the probe 11. The probe identification unit 26 identifies the type of the probe 11 on the basis of the input identification information.

The laser unit 13 includes, for example, a solid-state laser light source using a Q-switch which emits laser light and outputs laser light as measurement light L emitted to the subject M. For example, the laser unit 13 is configured such that it receives a trigger signal from a control unit 27 of the ultrasound unit 12 and outputs laser light. It is preferable that the laser unit 13 outputs pulsed light with a pulse width of 1 ns to 100 ns as the laser light. In this embodiment, the light source of the laser unit 13 is, for example, an alexandrite laser using a Q-switch.

The wavelength of the laser light is appropriately determined by the light absorption characteristics of an absorber in the subject to be measured. It is preferable that the wavelength of the laser light is a wavelength in the vicinity of a near-infrared wavelength range. For example, the wavelength of the laser light is in the range of 700 nm to 1200 nm. However, the wavelength of the laser light is not limited thereto. For example, visible light with a wavelength of 500 nm to 700 nm may be used. In addition, the laser light may have a single wavelength or may include a plurality of wavelengths (for example, 750 nm and 800 nm). In a case in which the laser light includes a plurality of wavelengths, light components with these wavelengths may be emitted to the subject M at the same time or may be emitted while being alternately switched. The laser unit 13 may use a Nd:YAG laser, a YAG-SHG-OPO laser, and a Ti-Sapphire laser that can output laser light in the near-infrared wavelength range and an SHG-Nd:YAG laser that can output laser light in the visible wavelength range, in addition to the alexandrite laser.

The ultrasound unit 12 comprises the receiving circuit 21, an analog-to-digital (AD) converter 22, a receiving memory 23, a photoacoustic image generation unit 24, a display control unit 25, the probe identification unit 26, and the control unit 27.

The ultrasound unit 12 is configured by, for example, a computer and typically includes a processor, a memory, and a bus. In the ultrasound unit 12, an embodiment of a photoacoustic image generation program according to the invention is installed in the memory. The control unit 27 configured by a processor executes the photoacoustic image generation program to implement the functions of the photoacoustic image generation unit 24, the display control unit 25, and the probe identification unit 26. That is, these units are configured by the processor and the memory into which the program is incorporated.

The hardware configuration of the ultrasound unit 12 is not particularly limited and can be implemented by an appropriate combination of, for example, a plurality of integrated circuits (ICs), a processor, an application specific integrated circuit (ASIC), a field-programmable gate array (FPGA), and a memory.

The receiving circuit 21 receives a photoacoustic wave detection signal output from the probe 11. The receiving circuit 21 typically includes a low-noise amplifier, a variable-gain amplifier, and a low-pass filter. The low-noise amplifier amplifies the photoacoustic wave detection signal output from the probe 11. Then, the variable-gain amplifier adjusts the gain of the photoacoustic wave detection signal according to the depth. Then, the low-pass filter cuts high-frequency components.

The AD converter 22 converts the photoacoustic wave detection signal received by the receiving circuit 21 into a digital signal. For example, the AD converter 22 samples the photoacoustic wave detection signal with a predetermined sampling period on the basis of a sampling clock signal with a predetermined period. The AD converter 22 stores the sampled photoacoustic wave detection signal (sampling data) in the receiving memory 23. For example, the receiving circuit 21 and the AD converter 22 may be configured as one IC or separate ICs.

Figure 2:
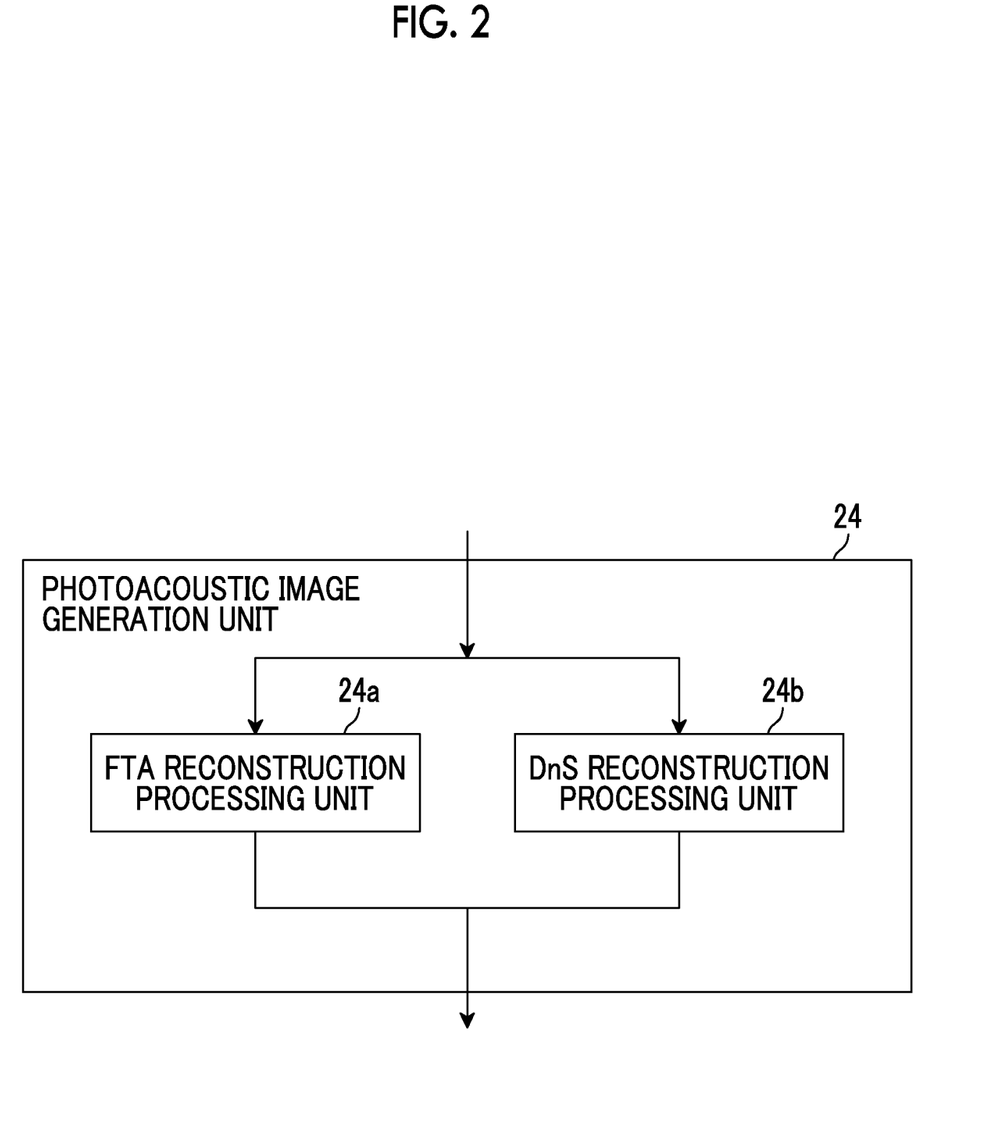
FIG. 2 is a block diagram illustrating a specific configuration of a photoacoustic image generation unit.

The photoacoustic image generation unit 24 generates a photoacoustic image on the basis of the photoacoustic wave detection signal stored in the receiving memory 23. The generation of the photoacoustic image includes, for example, a reconstruction process, detection, and logarithmic conversion. The photoacoustic image generation unit 24 according to this embodiment comprises an FTA reconstruction processing unit 24a and a DnS reconstruction processing unit 24b as illustrated in FIG. 2.

The FTA reconstruction processing unit 24a performs, as a frequency domain reconstruction process, a reconstruction process using an FTA method for the photoacoustic wave detection signal. The reconstruction process using the FTA method is a reconstruction processing method using the fact that measured time-space information can be converted into real-space information using a dispersion relation of sound waves in a frequency space. That is, first, two-dimensional forward Fourier transform is performed for a time series of the measured sound waves to acquire a time spectrum. Then, the time spectrum is converted into a space spectrum from the dispersion relation ($\omega=ck$, $\omega$: a time frequency, $k$: a spatial frequency) of the sound waves. Then, two-dimensional backward Fourier transform is performed to obtain a space distribution of a sound wave source as an image. In addition, the reconstruction process using the FTA method has been known from, for example, JP2010-035806A and "Photoacoustic Image Reconstruction-A Quantitative Analysis", Jonathan I. Sperl et al, SPIE-OSA Vol. 6631 663103". In this embodiment, the reconstruction process using the FTA method is used as the frequency domain reconstruction process. However, the invention is not limited thereto. Other reconstruction processes may be used as long as they can convert the measured time-space information into real-space information using the dispersion relation of the sound waves in the frequency space.

The DnS reconstruction processing unit 24b performs, as a time domain reconstruction process, a reconstruction process using a DnS method for the photoacoustic wave detection signal. The reconstruction process using the DnS method is a method which adds the detection signals of each ultrasound transducer while delaying the detection signals of the neighboring ultrasound transducers, considering a time difference until the sound waves emitted from the sound source reach each ultrasound transducer of the probe 11. In this embodiment, the reconstruction process using the DnS method is used as the time domain reconstruction process. However, the invention is not limited thereto. A reconstruction process using a convolution back projection (CBP) method may be used.

Figure 3:
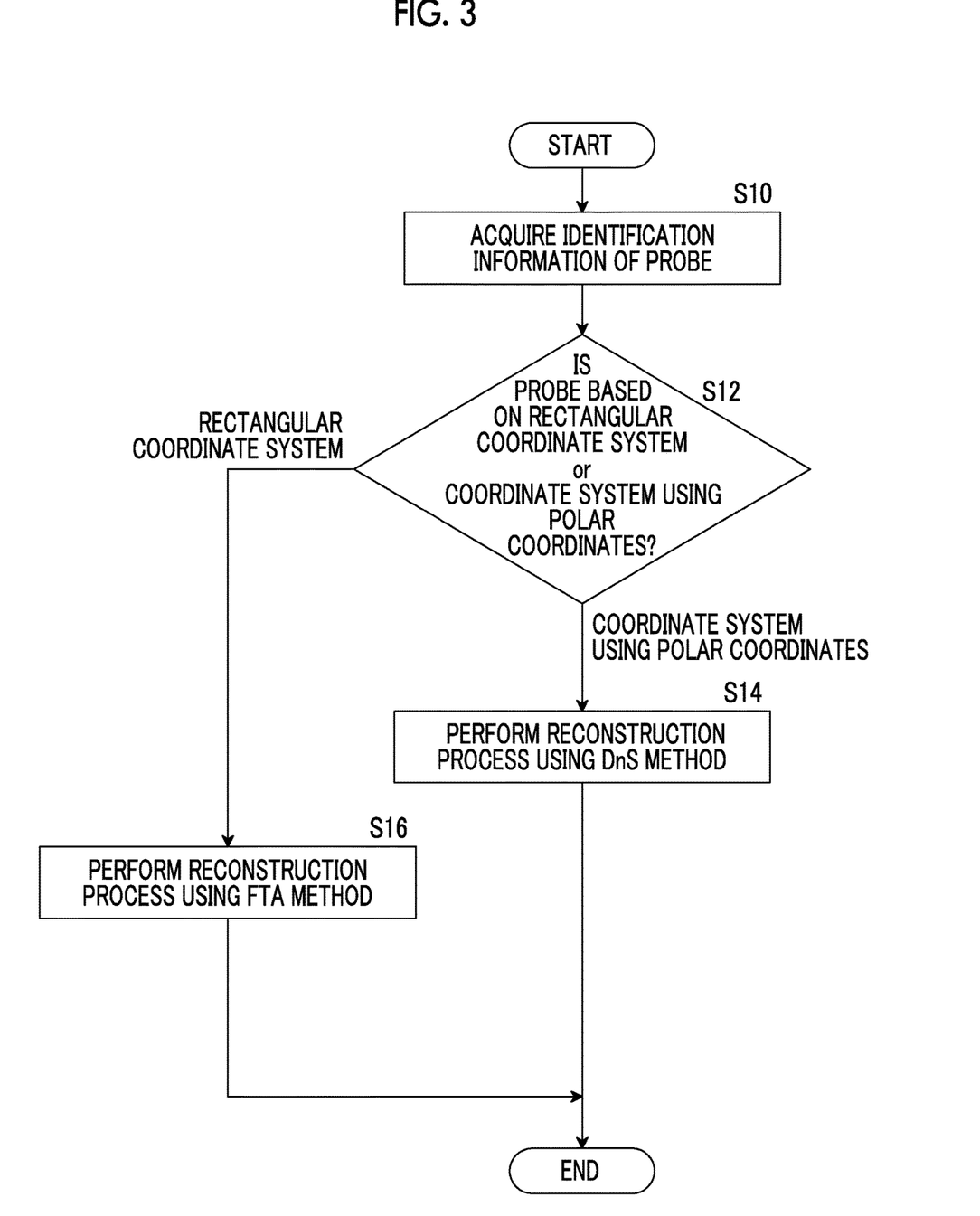
FIG. 3 is a flowchart illustrating an example of a reconstruction process selection method.

Then, the photoacoustic image generation unit 24 according to this embodiment selects one of the reconstruction process using the FTA method and the reconstruction process using the DnS method according to the probe 11 identified by the probe identification unit 26 and generates a photoacoustic image using the selected reconstruction process. FIG. 3 is a flowchart illustrating a reconstruction process selection method in the photoacoustic image generation unit 24.

As illustrated in FIG. 3, first, the probe identification unit 26 of the ultrasound unit 12 reads the identification information recorded on the probe information storage unit 11a and acquires the identification information (S10). Then, the probe identification unit 26 identifies whether the probe 11 connected to the ultrasound unit 12 is the probe based on the rectangular coordinate system or the probe based on the coordinate system using the polar coordinates, on the basis of the input identification information.

Then, the control unit 27 outputs a control signal to the photoacoustic image generation unit 24 on the basis of the identification result of the probe identification unit 26. The photoacoustic image generation unit 24 selects one of the reconstruction process using the FTA method and the reconstruction process using the DnS method on the basis of the input control signal.

Specifically, in a case in which the probe 11 connected to the ultrasound unit 12 is the probe based on the coordinate system using the polar coordinates (S12, a coordinate system using polar coordinates), the photoacoustic image generation unit 24 selects the reconstruction process using the DnS method from the reconstruction process using the FTA method and the reconstruction process using the DnS method and generates a photoacoustic image (S14). That is, in a case in which the probe 11 connected to the ultrasound unit 12 is, for example, a convex probe, a micro-convex probe, or a radial scanning probe, the photoacoustic image generation unit 24 generates a photoacoustic image with the reconstruction process using the DnS method.

In contrast, in a case in which the probe 11 connected to the ultrasound unit 12 is the probe based on the rectangular coordinate system (S12, a rectangular coordinate system), the photoacoustic image generation unit 24 selects the reconstruction process using the FTA method from the reconstruction process using the FTA method and the reconstruction process using the DnS method and generates a photoacoustic image (S16). That is, in a case in which the probe 11 connected to the ultrasound unit 12 is, for example, a linear probe and a sector probe, the photoacoustic image generation unit 24 generates a photoacoustic image with the reconstruction process using the FTA method.

In addition, it is preferable that the reconstruction process using the DnS method (time domain reconstruction process) in the DnS reconstruction processing unit 24b is not implemented by software (program), but is implemented by a hardware configuration such as a logic circuit. In contrast, it is preferable that the reconstruction process using the FTA method (frequency domain reconstruction process) in the FTA reconstruction processing unit 24a is implemented by a software process using a central processing unit (CPU) to which software (program) has been read or the CPU and a memory having the software stored therein rather than by a hardware configuration.

The reason is as follows. The reconstruction process using the DnS method is implemented by a hardware configuration in order to increase the processing speed. Since an arithmetic process is easy in the reconstruction process using the FTA method, it is possible to sufficiently increase the processing speed even in a case in which the reconstruction process using the FTA method is implemented by software.

Returning to FIG. 1, the control unit 27 controls each unit of the photoacoustic image generation apparatus 10 and comprises a trigger control circuit (not illustrated) in this embodiment. For example, in a case in which the photoacoustic image generation apparatus 10 operates, the trigger control circuit transmits a light emission trigger signal to the laser unit 13. Then, in the laser unit 13, a flash lamp is turned on and the excitation of a laser rod starts. Then, the excited state of the laser rod is maintained and the laser unit 13 can output pulsed laser light.

Then, in a case in which a photoacoustic image is generated, the control unit 27 transmits a Qsw trigger signal from the trigger control circuit to the laser unit 13. That is, the control unit 27 controls the output time of pulsed laser light from the laser unit 13 using the Qsw trigger signal. In addition, in this embodiment, the control unit 27 transmits a sampling trigger signal to the AD converter 22 at the same time as it transmits the Qsw trigger signal. The sampling trigger signal is a signal for the sampling start time of the photoacoustic wave detection signal in the AD converter 22. As such, the use of the sampling trigger signal makes it possible to sample the photoacoustic wave detection signal in synchronization of the output of laser light.

The display control unit 25 directs the display unit 14 to display the photoacoustic image generated by the photoacoustic image generation unit 24. For example, the display unit 14 displays the photoacoustic image and comprises a liquid crystal display. The input unit 15 receives various settings input by the user and comprises, for example, a keyboard and mouse.

The photoacoustic image generation apparatus 10 according to the above-described embodiment identifies whether the probe 11 is the probe based on the coordinate system using the polar coordinates or the probe based on the rectangular coordinate system. In a case in which it is identified that the probe 11 is the probe based on the coordinate system using the polar coordinates, the photoacoustic image generation apparatus 10 selects the time domain reconstruction process from the time domain reconstruction process and the frequency domain reconstruction process and generates a photoacoustic image. In a case in which it is identified that the probe 11 is the probe based on the rectangular coordinate system, the photoacoustic image generation apparatus 10 selects the frequency domain reconstruction process and generates a photoacoustic image. Therefore, it is possible to perform a more appropriate reconstruction process regardless of the type of probe, without causing a reduction in the speed of an arithmetic process.

In the photoacoustic image generation apparatus 10 according to the above-described embodiment, in a case in which the probe 11 connected to the ultrasound unit 12 is the probe based on the rectangular coordinate system, the photoacoustic image generation unit 24 automatically selects the reconstruction process using the FTA method and generates a photoacoustic image. However, the invention is not limited thereto. For example, as in a flowchart illustrated in FIG. 4, a configuration may be used in which the user selects one of the reconstruction process using the FTA method and the reconstruction process using the DnS method (S18). That is, a configuration may be used in which the user selects the reconstruction process in a case in which the probe 11 connected to the ultrasound unit 12 is, for example, a linear probe and a sector probe, as described above.

Figure 4:
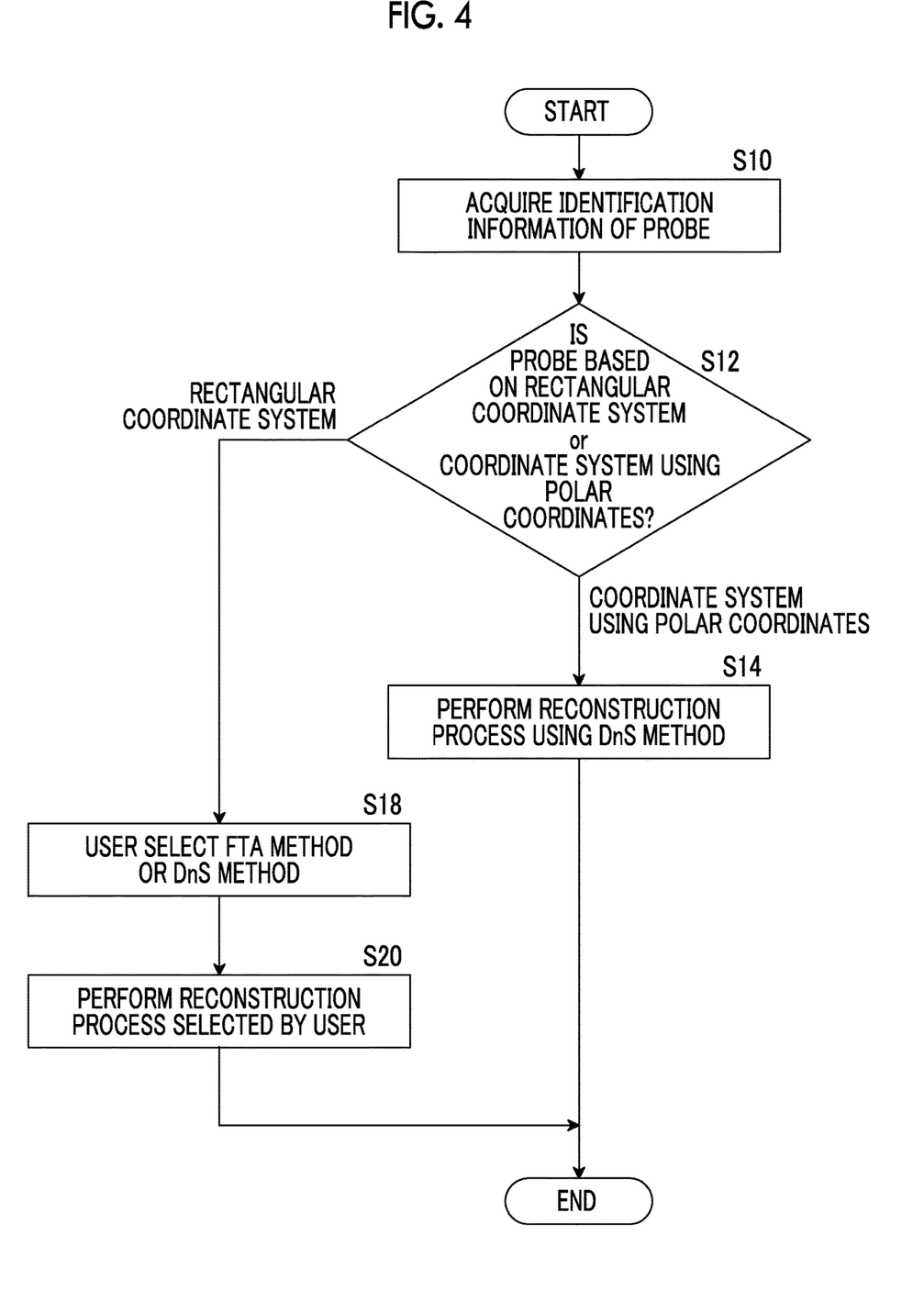
FIG. 4 is a flowchart illustrating another example of the reconstruction process selection method.

Then, in a case in which the probe 11 connected to the ultrasound unit 12 is the probe based on the rectangular coordinate system, a photoacoustic image may be generated using the reconstruction process selected by the user (S20). For the selection by the user, for example, a selection screen for receiving the selection of the reconstruction process may be displayed on the display unit 14 such that the user selects the reconstruction process with the input unit 15. In this case, the selection screen and the input unit 15 correspond to a reconstruction process selection receiving unit according to the invention.

In the photoacoustic image generation apparatus 10 according to the above-described embodiment, the probe 11 may transmit acoustic waves to the subject and each ultrasound transducer of the probe 11 may detect acoustic waves reflected from the subject with respect to the transmitted acoustic waves. Then, an ultrasound image (reflected wave image) may be generated on the basis of the reflected wave detection signal.

Figure 5:
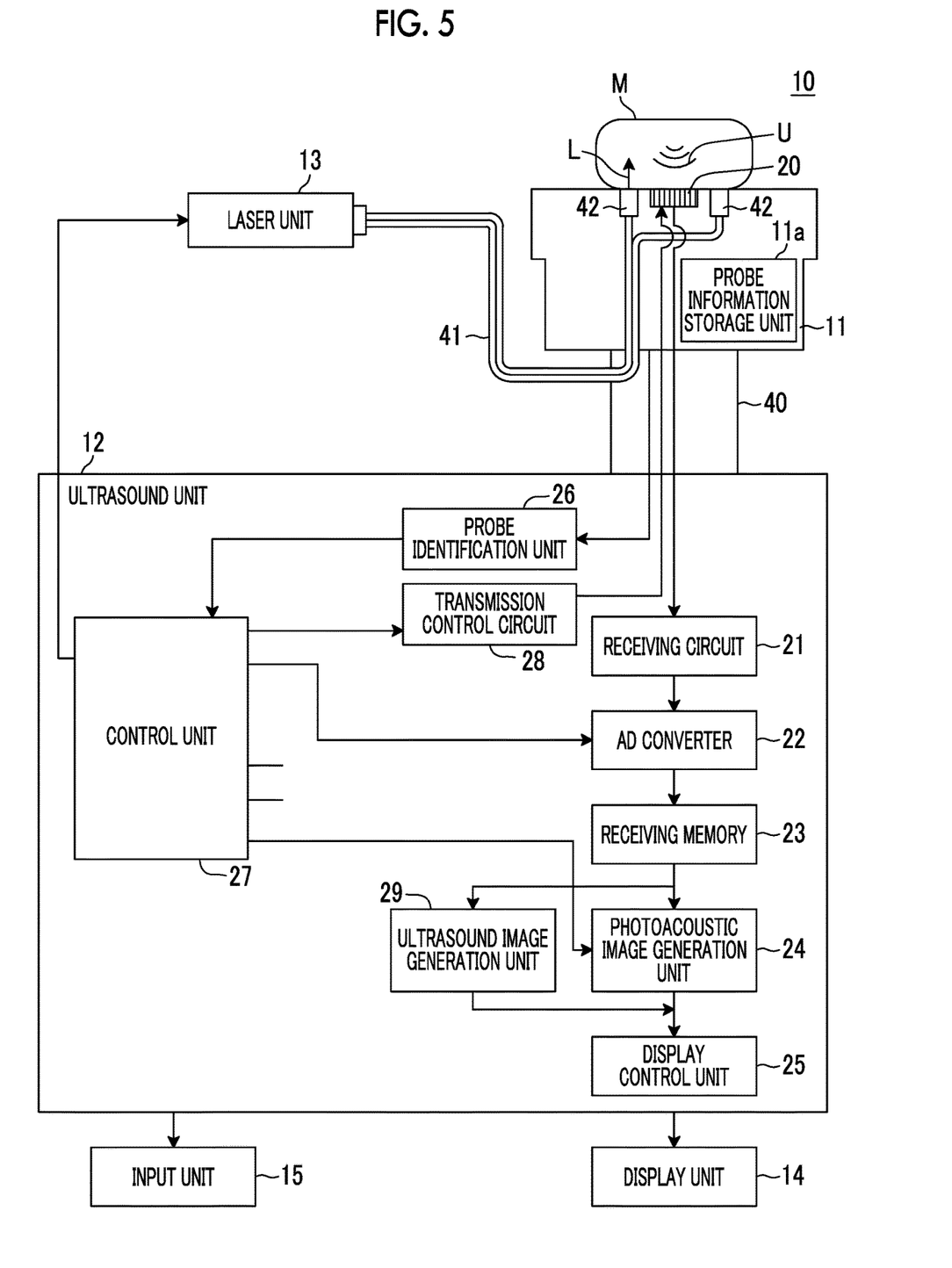
FIG. 5 is a block diagram schematically illustrating a configuration of another embodiment of the photoacoustic image generation apparatus according to the invention.

FIG. 5 is a block diagram illustrating the configuration of a photoacoustic image generation apparatus 10 including the generation of an ultrasound image. In this embodiment, ultrasonic waves are used as the acoustic waves. However, the acoustic waves are not limited to the ultrasonic waves. For example, acoustic waves with an audio frequency may be used as long as an appropriate frequency can be selected according to the subject to be examined or measurement conditions. In addition, the transmission and reception of the ultrasonic waves may be separated from each other. For example, ultrasonic waves may be transmitted from a position different from the position of the probe 11 and the probe 11 may receive reflected ultrasonic waves with respect to the transmitted ultrasonic waves.

In a case in which an ultrasound image is generated, the control unit 27 of the photoacoustic image generation apparatus 10 illustrated in FIG. 5 transmits an ultrasonic wave transmission trigger signal for commanding the transmission of ultrasonic waves to a transmission control circuit 28. In a case in which the trigger signal is received, the transmission control circuit 28 directs the probe 11 to transmit ultrasonic waves. The probe 11 transmits ultrasonic waves, detects ultrasonic waves reflected from the subject M, and outputs a reflected wave detection signal.

The reflected wave detection signal output from the probe 11 is input to the AD converter 22 through the receiving circuit 21. The control unit 27 transmits a sampling trigger signal to the AD converter 22 in synchronization of the transmission time of the ultrasonic waves to start the sampling of the reflected wave detection signal. Then, the AD converter 22 stores the sampled reflected wave detection signal in the receiving memory 23.

An ultrasound image generation unit 29 generates an ultrasound image on the basis of the reflected wave detection signal stored in the receiving memory 23. The generation of the ultrasound image includes a reconstruction process, detection, and logarithmic conversion. It is preferable that the reconstruction process of the ultrasound image generation unit 29 is the reconstruction process using the DnS method. In addition, it is preferable that the ultrasound image generation process of the ultrasound image generation unit 29 is not implemented by software (program), but is implemented by a hardware configuration such as a logic circuit. The ultrasound image generation unit 29 corresponds to a reflected wave image generation unit.

In the above-described embodiment, for the photoacoustic image generation process of the photoacoustic image generation unit 24, the reconstruction process using the FTA method is implemented by a software process and the reconstruction process using the DnS method is implemented by a hardware configuration such as a logic circuit. However, the reconstruction process using the DnS method may also be implemented by a software process. That is, the photoacoustic image generation process of the photoacoustic image generation unit 24 may be implemented by a software process using a central processing unit (CPU) to which software (program) has been read or the CPU and a memory having the software stored therein. As such, in a case in which the photoacoustic image generation process is implemented by a software process, for example, it is possible to generate a photoacoustic image by adding software to the existing ultrasound image generation apparatus that generates only an ultrasound image. Therefore, it is possible to easily improve the design without greatly changing the configuration of the apparatus.

The ultrasound image generated by the ultrasound image generation unit 29 is output to the display control unit 25 and the display control unit 25 directs the display unit 14 to display the input ultrasound image. In addition, a photoacoustic image and an ultrasound image may be separately displayed or a composite image obtained by superimposing the photoacoustic image and the ultrasound image may be generated and displayed.

The invention has been described above with reference to the preferred embodiments. The photoacoustic image generation apparatus according to the invention is not limited only to the above-described embodiments and various modifications and changes in the configurations of the above-described embodiments are also included in the scope of the invention.

EXPLANATION OF REFERENCES

10: photoacoustic image generation apparatus
11: probe
11a: probe information storage unit
12: ultrasound unit
13: laser unit
14: display unit
15: input unit
20: transducer array
21: receiving circuit
22: AD converter
23: receiving memory
24: photoacoustic image generation unit
24a: FTA reconstruction processing unit
24b: DnS reconstruction processing unit
25: display control unit
26: probe identification unit
27: control unit
28: transmission control circuit
29: ultrasound image generation unit
40: cable
41: bundle fiber
42: light emission portion
L: measurement light
M: subject
U: photoacoustic wave

What is claimed is:

1. A photoacoustic image generation apparatus comprising:
   a probe that detects photoacoustic waves generated in a subject irradiated with light and outputs a photoacoustic wave detection signal, and that stores identification information of the probe; and
   a processor configured to:
      identify whether the probe is a probe in which detection elements are arranged by a coordinate system using polar coordinates or a probe in which detection elements are arranged by a rectangular coordinate system, by reading the identification information of the probe in response to a request signal; and
      in a case in which the probe is identified as the probe in which the detection elements are arranged by the coordinate system using the polar coordinates. select and perform a time domain reconstruction process and generate a photoacoustic image based on the time domain reconstruction process; and
      in a case in which the probe is identified as the probe in which the detection elements are arranged by the rectangular coordinate system, select and perform a the-frequency domain reconstruction process and generate a photoacoustic image based on frequency domain reconstruction process.

2. The photoacoustic image generation apparatus according to claim 1,
   wherein the processor is configured to identify at least one of a convex probe, a micro-convex probe, or a radial scanning probe as the probe in which the detection elements are arranged by the coordinate system using the polar coordinates.

3. The photoacoustic image generation apparatus according to claim 2,
   wherein the processor is configured to identify at least one of a linear probe or a sector probe as the probe in which the detection elements are arranged by the rectangular coordinate system.

4. The photoacoustic image generation apparatus according to claim 3,
   wherein the time domain reconstruction process is a reconstruction process using a delay-and-sum method.

5. The photoacoustic image generation apparatus according to claim 3,
   wherein the time domain reconstruction process is a reconstruction process using a convolution back projection method.

6. The photoacoustic image generation apparatus according to claim 2,
   wherein the time domain reconstruction process is a reconstruction process using a delay-and-sum method.

7. The photoacoustic image generation apparatus according to claim 6,
   wherein the time domain reconstruction process is a reconstruction process using a convolution back projection method.

8. The photoacoustic image generation apparatus according to claim 2,
   wherein the time domain reconstruction process is a reconstruction process using a convolution back projection method.

9. The photoacoustic image generation apparatus according to claim 1, wherein the processor is configured to identify at least one of a linear probe or a sector probe as the probe in which the detection elements are arranged by the rectangular coordinate system.

10. The photoacoustic image generation apparatus according to claim 9,
wherein the time domain reconsruction process is a reconstruction process using a delay-and-sum method.

11. The photoacoustic image generation apparatus according to claim 9,
wherein the time domain reconstruction process is a reconstruction process using a convolution back projection method.

12. The photoacoustic image generation apparatus according to claim 1,
wherein the time domain reconstruction process is a reconstruction process using a delay-and-sum method.

13. The photoacoustic image generation apparatus according to claim 5,
wherein the time domain reconstruction process is a reconstruction process using a convolution back projection method.

14. The photoacoustic image generation apparatus according to claim 1,
wherein the time domain reconstruction process is a reconstruction process using a convolution back projection method.

15. The photoacoustic image generation apparatus according to claim 1,
wherein the frequency domain reconstruction process is a reconstruction process using a Fourier transform algorithm method.

16. The photoacoustic image generation apparatus according to claim 1,
wherein the probe detects reflected waves of acoustic waves transmitted to the subject and outputs a reflected wave detection signal, and
wherein the processor is configured to perform the reconstruction process using the delay-and-sum method on the basis of the reflected wave detection signal to generate a reflected wave image.

17. The photoacoustic image generation apparatus according to claim 16,
wherein the processor is configured to implement a process of generating the reflected wave image using hardware, and
implement a process of generating the photoacoustic image using software.

18. The photoacoustic image generation apparatus according to claim 1,
wherein the processor is configured to implement the time domain reconstruction process using hardware and implement the frequency domain reconstruction process using software.

19. A photoacoustic image generation method that performs a time domain reconstruction process or a frequency domain reconstruction process, using a photoacoustic wave detection signal obtained by detecting photoacoustic waves generated in a subject irradiated with light, to generate a photoacoustic image, the method comprising:
identifying whether a probe that detects the photoacoustic waves and outputs the photoacoustic wave detection signal and that stores identification information of the probe is a probe in which detection elements are arranged by a coordinate system using polar coordinates or a probe in which detection elements are arranged by a rectangular coordinate system, by reading the identification information of the probe in response to a request signal;
in a case in which the probe is identified as the probe in which the detection elements are arranged by the coordinate system using the polar coordinates, selecting and performing the time domain reconstruction process and generating a photoacoustic image based on the time domain reconstruction process; and
in a case in which the probe is identified as the probe in which the detection elements are arranged by the coordinate system using the rectangular coordinates, selecting and performing the frequency domain reconstruction process and generating a photoacoustic image based on the frequency domain reconstruction process.

20. A recording media storing non-transitory computer readable photoacoustic image generation program that causes a computer to function as:
identifying whether a probe that detects photoacoustic waves and outputs the photoacoustic wave detection signal and that stores identification information of the probe is a probe in which detection elements are arranged by a coordinate system using polar coordinates or a probe in which detection elements are arranged by a rectangular coordinate system, by reading the identification information of the probe in response to a request signal;
in a case in which the probe is identified as the probe in which the detection elements are arranged by the coordinate system using the polar coordinates, selecting a time domain reconstruction process, performing the time domain reconstruction process using a photoacoustic wave detection signal obtained by detecting photoacoustic waves generated in a subject irradiated with light, and generating a photoacoustic image based on the time domain reconstruction process; and
in a case in which the probe is identified as the probe in which the detection elements are arranged by the rectangular coordinate system selecting a frequency domain reconstruction process, performing the frequency domain reconstruction process using the photoacoustic wave detection signal obtained by detecting photoacoustic waves generated in the subject irradiated with light, and generating a photoacoustic image based on the frequency domain reconstruction process.

* * * * *